United States Patent [19]

Portnoy

[11] Patent Number: 4,530,663
[45] Date of Patent: * Jul. 23, 1985

[54] DENTURE MAGNETIC RETENTION UNIT

[76] Inventor: Leonard L. Portnoy, 8820 Wilshire Blvd., Suite 303, Beverly Hills, Calif. 90211

[*] Notice: The portion of the term of this patent subsequent to Feb. 14, 2001 has been disclaimed.

[21] Appl. No.: 630,675

[22] Filed: Jul. 13, 1984

[51] Int. Cl.³ .............................................. A61C 13/22
[52] U.S. Cl. .................................................... 433/189
[58] Field of Search ................................. 433/189, 60

[56] References Cited

U.S. PATENT DOCUMENTS

| 3,646,676 | 3/1972 | Mitchell | 433/189 |
| 4,209,905 | 7/1980 | Gillings | 433/189 |
| 4,302,189 | 11/1981 | Gillings | 433/189 |
| 4,431,419 | 2/1984 | Portnoy | 433/189 |

Primary Examiner—John J. Wilson
Attorney, Agent, or Firm—Keith D. Beecher

[57] ABSTRACT

A closed field magnetic denture retention unit which includes a ferromagnetic cup containing a cylindrical permanent magnet, the cup and magnet being embedded in the denture; and a magnetic keeper which is embedded in an exposed tooth root in the mouth of a patient and extends across the top of the cup to close the magnetic field when the denture is in place. The unit serves to retain the denture in place by magnetic attraction, the keeper forming a closed magnetic field so that there is not external magnetic field in the mouth of the patient.

7 Claims, 9 Drawing Figures

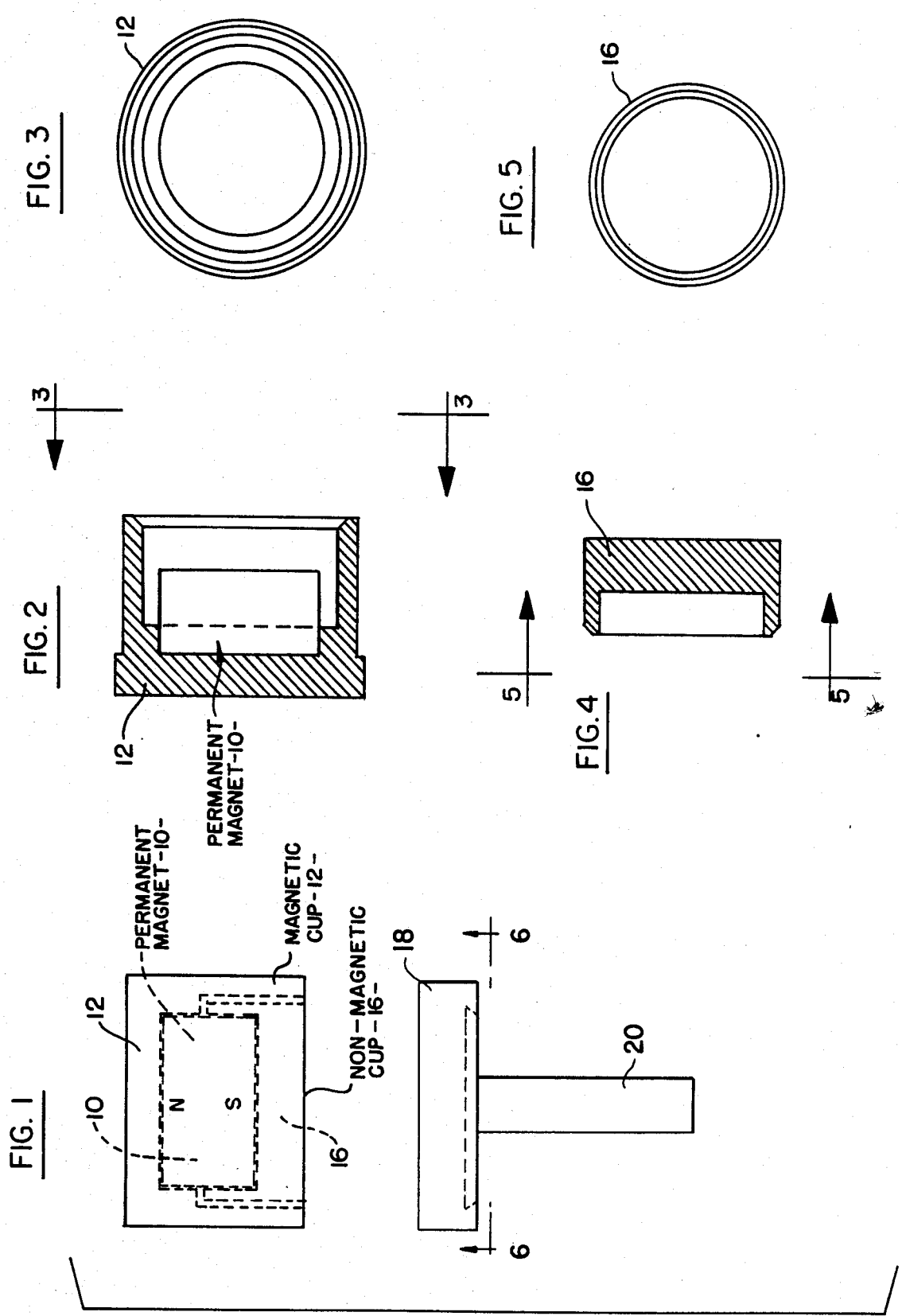

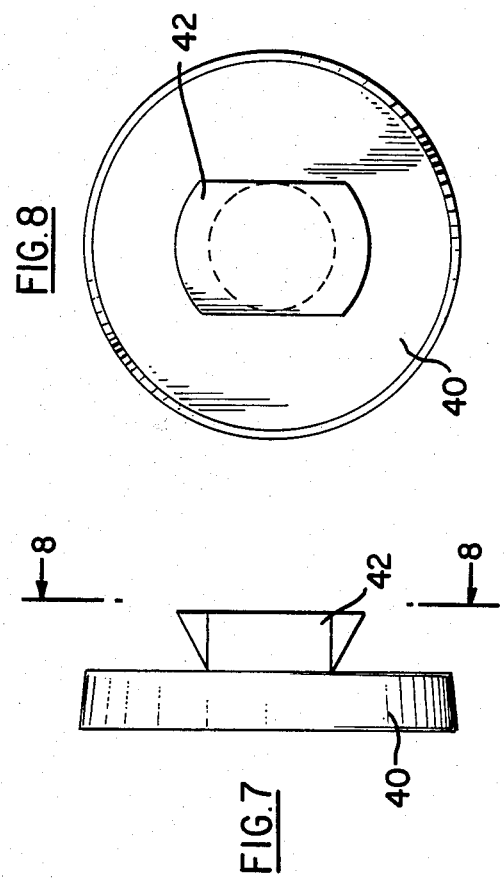
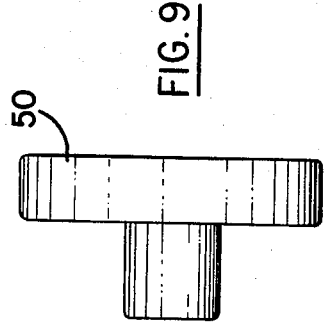
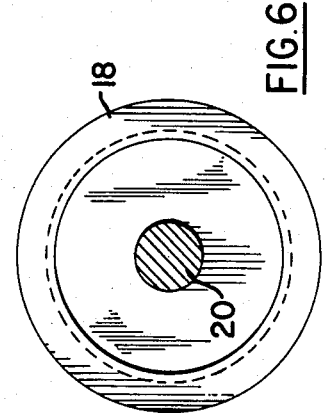

DENTURE MAGNETIC RETENTION UNIT

BACKGROUND OF THE INVENTION

Magnetic denture retention devices have been developed by Dr. Barrie R. D. Gillings of the Univeristy of Malaya in Malaysia, these being described in his U.S. Pat. Nos. 4,209,905 and 4,302,189. The use of permanent magnets as denture retention devices is described in various publications by Dr. Gillings. For example, paired bar permanent magnets, embedded into the maxillary and mandibular dentures, have been used for denture retention, through the mutual repulsion of like poles of the magnets. Permanent magnets have also been used as implants in the bone of the lower jaw as retention aids for mandibular dentures containing opposite polarity magnets, so that magnetic attraction will occur between the implanted magnets and the magnets in the dentures.

Recently, a new magnetic alloy, composed of cobalt and samarium ($CO_5Sm$) has become available. Permanent magnets made from this alloy not only exhibit extremely high magnetic field strength, but they also possess extremely high coercivity. This coercivity is so high in cobalt/samarium magnets that the magnets can be made extremely short without the north pole tending to demagnetize the south pole. This unique property is such that cylindrical-shaped permanent magnets of a diameter, for example, of 3 millimeters, and of a length of 2 to 3 millimeters, can provide magnetic attraction forces in excess of 300 grams. This property of the cobalt/samarium magnet renders it ideal for use in the unit of the present invention.

It is widely believed that the magnetic fields produced by permanent magnets can damage tissues, when such magnets are used in patients' mouths. This belief has inhibited the use of permanent magnets for denture retention purposes in the past. However, Dr. Gillings in the publications referred to above describes magnetic type denture retention units which do not exhibit any significant external magnetic field, so as to remove any objection to the use of his devices for denture retention purposes.

The Gillings closed field magnetic retention unit comprises a pair of oppositely-poled permanent magnets, preferably of the cobalt/samarium type placed adjacent to one another in a slightly spaced relationship. A first ferromagnetic keeper is placed across one end of the two magnets in contact with the magnets to form a first magnetic path between the opposite poles of the two magnets at that end. In accordance with Dr. Gillings' teachings, the two magnets and the first keeper are embedded in the denture with the two pole faces at the opposite ends of the magnets being exposed at the surface of the denture. A second keeper of ferromagnetic material is embedded in the root in the patient's mouth which is to serve as an anchor for the denture. When the denture is in place, it is magnetically retained on the root because of the magnetic attraction of the second keeper and the permanent magnets. Moreover, the resulting assembly produces a closed magnetic circuit from the poles of the permanent magnets through the two keepers, so that there is no external magnetic field.

U.S. Pat. No. 4,431,419 which issued Feb. 14, 1984 in the name of the present inventor discloses a unit which achieves the same results as the Gillings' unit, but which may be more simply constructed than the Gillings' unit, and which has inherent features where are not present in the Gillings' unit. The present invention constitutes a further improvement over the unit disclosed in U.S. Pat. No. 4,431,419.

BRIEF DESCRIPTION OF THE DRAWINGS

FIG. 1 is an elevational representation, partly in section, of the magnetic denture retention unit of the present invention in one of its embodiments including a permanent magnet assembly which is embedded in the denture, and a direct keeper which is mounted on a tooth of the patient;

FIG. 2 is a side section of one of the components of the permanent magnet assembly of FIG. 1;

FIG. 3 is a view of the component of FIG. 2, taken essentially along the lines 3—3 of FIG. 1;

FIG. 4 is a side section of another of the components of the permanent magnet assembly of FIG. 1;

FIG. 5 is a view of the component of FIG. 4, taken essentially along the lines 5—5 of FIG. 4;

FIG. 6 is a bottom view of the keeper of FIG. 1, taken along the line 6—6 of FIG. 1;

FIG. 7 is a side view of an indirect keeper for use with the permanent magnet assembly of FIG. 1;

FIG. 8 is a bottom view of the keeper of FIG. 7; and

FIG. 9 is a side view of a transfer keeper for use with the permanent magnet assembly of FIG. 1.

DETAILED DESCRIPTION OF THE ILLUSTRATED EMBODIMENT

Although many researchers believe that magnetic fields have no adverse affect on human tissues and that magnetism is completely innocuous to tissues, there is a considerable body of literature suggesting that magnetic fields can exert adverse tissue effects.

In some of the prior art magnetic denture retention units, an external magnetic field is generated which may be as high as 30 milliteslas at the gingival margin, which some investigators believe to be too high for permanent clinical applications.

In the magnetic unit of the present invention, as shown in FIG. 1, a closed magnetic field is obtained by use of a simple cylindrical permanent magnet 10, which is retained in a cup 12 by a press fit into a reduced diameter pocket formed in the bottom of the cup. The magnet 10 may be composed, for example, of a cobalt/samarium alloy. The cup 12 may be formed of any appropriate magnetic material of low coercivity, such as ferromagnetic stainless steel, for example, of the 400 Series. As shown, the permanent magnet in FIG. 2 is poled to have a north pole at one end of a south pole at the other end, although the polarity may be reversed if so desired. The permanent magnet 10 is in direct contact with the bottom of the cup 12, and the portion of the magnet extending out of the pocket is spaced from the inner surface of the cup. The top end of the permanent magnet is displaced down from the rim of cup 12.

A second cup 16 of non-magnetic material extends in a press-fit into cup 12 as shown, to retain the magnet 10 in the cup 12.

The first component of the unit of the invention, namely the cups 12, and 16, and magnet 10, are embedded in the denture to be retained in the mouth of the patient. A second component of the unit, namely a direct magnetic keeper 18 is mounted on an exposed root in the mouth of the patient, which is intended to anchor the denture in place. The magnetic keeper 18 has a stem 20 which extends into a channel formed in the root. The keeper is cemented in place by suitable adhesive which covers the stem and the keeper. An undercut cut-out-section may be provided on the underside of the keeper as indicated by the broken line and a quantity of the adhesive extends into the cut-out section to assist in anchoring the keeper to the tooth. The keeper 18 is also formed of low coercivity magnetic material, such as ferromagnetic stainless steel of the 400 Series.

The diameter of the keeper 18 is such that it extends across the end of cup 12 to engage the peripheral edge of the cup 12. The keeper 18 is spaced from the permanent magnet 10, by the non-magnetic cup 16. The spacing may be increased or decreased by selecting the length of the permanent magnet, so as to achieve any desired magnetic strength for the retention unit.

When the denture is in place, the magnet 10 is completely enclosed in the magnetic cup 12 by the keeper 18. The cup and the keeper form a low reluctance magnetic path for the magnetic field of the permanent magnet, so that the field is completely enclosed, and there is no external field to affect the tissues in the mouth of the patient.

An indirect keeper 40 is shown in FIGS. & and 8, and it too is formed of appropriate magnetic material such as #416 stainless steel. The indirect keeper 40 is embedded in non-magnetic metal post which is cemented over the tooth as a mount for the keeper 40. Keeper 40 is equipped with a tab 42 which serves to position the keeper in the mold during the casting of the metal post. The tab is subsequently removed.

If desired, the post itself may be made of magnetic material and may act itself as a keeper, thereby obviating any need for the keeper 40.

A transfer keeper 50 (FIG. 8) formed of suitable magnetic material, such as #416 stainless steel when the denture is made from a model of the mouth of the patient. The keeper is temporarily mounted in the model to hold the permanent magnet assembly in place in the denture impression.

The invention provides, therefore, a simple magnetic retention unit for retaining dentures in the mouth of the patient, which can be assembled from readily available components, and which is simple to install in the denture and in the mouth of the patient.

It will be appreciated that while a particular embodiment of the invention has been shown and described, modifications may be made, and it is intended in the claims to cover all modifications which come within the true spirit and scope of the invention.

What is claimed is:

1. A denture magnetic retention unit comprising: a first component in the form of a first cup-shaped member of magnetic material having an open top, a permanent magnet positioned within said first cup-shaped member, and a second cupshaped member of non-magnetic material extending into said first cup-shaped member to retain the magnet in said first cup-shaped member; and a second component in the form of a keeper of magnetic material positioned to extend across the open top of said cup-shaped member to close the magnetic field with said open top when the denture is in place.

2. The denture magnetic retention unit defined in claim 1, in which said magnet is mounted in a pocket formed in the bottom of said first cup-shaped member, and said second cup-shaped member extends between the external surface of the magnet and the internal surface of said first cup-shaped member in press-fit with said first cup-shaped member.

3. The denture magnetic retention unit defined in claim 1, in which said first component is adapted to be embedded in the denture, and said second component is adapted to be embedded in an exposed root of a tooth in the mouth of a patient.

4. The denture magnetic retention unit defined in claim 1, in which said first cup-shaped member and said keeper are formed of a ferromagnetic stainless steel.

5. The denture magnetic retention unit defined in claim 1, in which the permanent magnet has a disc shape with magnetic poles on opposite sides thereof, and with one side of said disc-shaped permanent magnet contacting the bottom of the first cup-shaped member.

6. The denture magnetic retention unit defined in claim 5, in which the other side of the disc-shaped permanent magnet is displaced inwardly from the top of said first cup-shaped member.

7. The denture magnetic retention unit defined in claim 1, in which the permanent magnet is a cobalt-/samarium alloy.

* * * * *